United States Patent [19]

Rattner

[11] Patent Number: 5,233,972
[45] Date of Patent: Aug. 10, 1993

[54] SHOCKWAVE SOURCE FOR ACOUSTIC SHOCKWAVES

[75] Inventor: Manfred Rattner, Grossenseebach, Fed. Rep. of Germany

[73] Assignee: Siemens Aktiengesellschaft, Munich, Fed. Rep. of Germany

[21] Appl. No.: 758,755

[22] Filed: Sep. 12, 1991

[30] Foreign Application Priority Data

Sep. 27, 1990 [EP] European Pat. Off. ........ 90118601.5

[51] Int. Cl.$^5$ .............................................. A61B 17/22
[52] U.S. Cl. ................................ 128/24 EL; 367/174
[58] Field of Search ................ 128/24 EL, 660.03; 367/174, 175, 182–187

[56] References Cited

U.S. PATENT DOCUMENTS

| | | |
|---|---|---|
| 4,697,588 | 10/1987 | Reichenberger . |
| 4,782,471 | 11/1988 | Klein ................................. 367/174 |
| 4,782,821 | 11/1988 | Reitter ............................ 128/24 EL |
| 4,793,329 | 12/1988 | Mahler et al. . |
| 4,796,608 | 1/1989 | Koehler . |
| 4,807,627 | 2/1989 | Eisenmenger ................. 128/24 EL |
| 4,821,245 | 4/1989 | Riedlinger . |
| 4,901,709 | 2/1990 | Rattner ........................... 128/24 EL |
| 4,920,955 | 5/1990 | Mahler et al. ...................... 367/175 |
| 4,924,858 | 5/1990 | Katona ................................. 367/175 |

FOREIGN PATENT DOCUMENTS 10926 4/1924 Netherlands .

Primary Examiner—Lee S. Cohen
Assistant Examiner—Samuel Gilbert
Attorney, Agent, or Firm—Hill, Steadman & Simpson

[57] ABSTRACT

An electromagnetic or electrodynamic shockwave source for generating acoustic shockwaves has a movable element which can be driven for generating the shockwaves, and a stationary element which is in electromagnetic interaction with the movable element to drive the movable element. A membrane which contains an electrical coil arrangement, the coil being charged with high-voltage pulses to cause the generation of shockwaves, is provided as the movable element. A component containing electrically conductive material is disposed opposite the coil arrangement, and is provided as the stationary element.

19 Claims, 4 Drawing Sheets

SHOCKWAVE SOURCE FOR ACOUSTIC SHOCKWAVES

BACKGROUND OF THE INVENTION

1. Field of the Invention

The present invention is directed to an electromagnetic or electrodynamic shockwave source for generating acoustic shockwaves, of the type having a movable element which is driven for generating shockwaves, and a stationary element in electromagnetic interaction with the movable element for driving the movable element.

2. Description of the Prior Art

Electromagnetic or electrodynamic shockwaves wherein the shockwaves are generated by a movable element driven by electromagnetic interaction with a stationary element, are used in medical technology, for example for the non-invasive disintegration of calculi, for treating pathological tissue conditions, or for treating bone conditions. Such a shock wave source is disclosed in European Application 0 188 750, corresponding to U.S. Pat. No. 4,697,588. The shockwave source disclosed therein has a coil arrangement which serves as the stationary element, and which is attached to an insulator member in the shockwave source. A membrane of electrically conductive material is employed as the movable element, and is disposed opposite the stationary coil arrangement. When the coil arrangement is charged with a high-voltage pulse, currents are induced in the membrane in a direction opposite to the direction of the current flowing in the coil arrangement. As a consequence of the opposite magnetic fields arising due to the respective flows of current in the coil arrangement and in the membrane, the membrane is subjected to repelling forces which suddenly and rapidly move the membrane away from the coil. A pressure pulse is thereby introduced into an acoustic propagation medium disposed adjacent the membrane. This pressure pulse intensifies during its path through the propagation medium to form a shockwave, as a consequence of the non-linear compression properties of the propagation medium. For simplicity, the waves in the propagation medium will always be referred to herein as shockwaves, and this term will encompass incipient shockwaves in the form of pressure pulses.

When necessary, the shockwaves are concentrated onto a focal zone using suitable focusing means, for example an acoustic lens, or by shaping the shockwave source by fashioning the membrane and the coil arrangement as a portion of a sphere. The shockwave source and the subject to be acoustically irradiated are acoustically coupled to each other in a suitable manner, and are aligned relative to each other so that the region to be acoustically irradiated is situated in the focal zone.

In known shockwave sources of this type, the coil arrangement is in the form of a spiral coil, the turns of the spiral coil being connected to an insulator member by gluing. The glued connection between the coil and the insulator member is subjected to high mechanical stress, because pressure waves are also generated in the insulator member as a consequence of the repelling forces acting between the coil arrangement and the membrane when the shockwaves are generated. These pressure waves are reflected at the rear side of the insulator member, facing away from the coil arrangement, with an inversion of the operational sign, as rarefaction (i.e., negative pressure) waves. There is therefore the risk that the coil arrangement will become detached from the insulator member, which has the consequence of heat elimination from the coil into the insulator member being disrupted, and only shockwaves having largely diminished peak pressure can then be generated. Moreover, there is the risk that the coil arrangement and the membrane will be destroyed due to punctures caused by electrical arcing in the event of a detachment of the coil arrangement from the insulator member.

SUMMARY OF THE INVENTION

It is an object of the present invention to provide an electromagnetic or electrodynamic shockwave source wherein damage to the shockwave source, and in particular to the coil arrangement, due to pressure waves reflected at a rear side of the stationary element is avoided.

The above object is achieved in accordance with the principles of the present invention in a shockwave source having a movable element which is driven for generating shockwaves and a stationary element which electromagnetically interacts with the movable element wherein the movable element is a membrane containing the electrical coil arrangement, and the stationary element is a component disposed opposite the coil arrangement which contains electrically conductive material. In contrast to conventional shockwave sources, wherein the coil is stationary and the membrane containing electrically conductive material is movable, in the shockwave source disclosed herein the coil arrangement is movable and the membrane is stationary. When the coil arrangement in the shockwave source disclosed herein is charged with high-voltage pulses, currents are induced in the stationary element of the shockwave source, which causes the coil arrangement, and the flexible membrane in which it is embedded, to be repelled together from the stationary element. As in known shockwave sources, pressure waves are introduced into the stationary element, which are reflected as rarefaction waves at the rear side of the stationary element. In the shockwave source disclosed herein, however, because the coil arrangement is not connected to the stationary element, these rarefaction waves (which are reflected again, with another inversion of operational sign, at the front side of the stationary element adjacent the membrane containing the coil) cannot cause any damage.

The membrane containing the coil arrangement can be constructed in a technically simple and economic manner in the form of an insulator carrying the windings forming the coil as an electrically conductive layer. Such a membrane can be manufactured using photolithographic methods, similar to the manufacture of a printed circuit composed of a plastic foil or plate laminated to an electrically conductive layer, for example to a copper layer.

In a preferred embodiment of the invention the coil arrangement has a plurality of windings which are electrically insulated from each other and are connected in parallel to each other, and the membrane has a plurality of layers each having a winding therein. As a result of the layered structure of the coil arrangement contained in the membrane, an improved electromagnetic interaction with the stationary element is achieved, due to the generation of an electromagnetic field having field lines which are curved in a in a more beneficial manner, particularly having lower scatter than in conventional devices. The improved electromagnetic interaction is in the form of an intensification of the repelling forces which occur between the coil arrangement contained in the membrane and the stationary element, so that an improved efficiency is achieved in the conversion of electrical energy into acoustic shock energy.

A further improvement in the electromagnetic interaction, and thus in the efficiency, is possible in an embodiment wherein the turns of the winding of a layer of the coil arrangement at least partially overlap the spaces between the turns of the winding in the immediately adjacent layer. This achieves the generation of an extremely uniform and low-scatter electromagnetic field. A further reduction in the inhomogeneities of the electromagnetic field generated with the coil arrangement, and thus a further increase in efficiency, can be achieved by arranging the turns of the windings of a plurality of successive layers in spirals, with the windings of the layers being offset relative to each other so that the turns of the spiral winding of one layer overlap the spiral spaces between the turns of the winding of the immediately adjacent layer.

In an advantageous embodiment of the invention, the stationary element contains electrically conductive material in the form of electrically conductive sections which are electrically insulated from each other and which are arranged in a plurality of layers, at least in the region of the stationary element adjacent to the coil arrangement. Similar to the case of the coil arrangement, an improved electromagnetic interaction is also achieved by the layered structure of the stationary element, resulting in the generation of higher repelling forces and an improved efficiency.

For avoiding voltage arcing between the coil arrangement and the electrically conductive material contained in the stationary element, an improvement in the electrical strength of the shockwave source can be achieved in an embodiment of the invention wherein the electrically conductive sections of one layer of the stationary element at least partially overlap the spaces between the electrically conductive sections of at least the immediately adjacent layer of the stationary element. A capacitive coupling of the electrically conductive sections to each other is achieved in this manner, which results in the overall operating voltage of the shockwave source being uniformly divided into differences in potential between the individual, electrically conductive sections. The differences in potential are not only present between the electrically conductive sections within the stationary element, but are also present between the electrically conductive sections of the stationary element and the portion or region of the coil arrangement which is close to the stationary element. These differences in potential are so small that the risk of voltage arcing is substantially suppressed. Under certain circumstances, a reduction in the distance between the coil arrangement contained in the membrane and the electrically conductive material contained in the stationary element is possible, which results in the advantage of a further improvement in efficiency. An especially good capacitive coupling, and thus especially uniform differences in potential, can be achieved in an embodiment wherein a plurality of successive layers of the stationary element have electrically conductive sections in the form of concentric rings, and the concentric rings of the layers are offset relative to each other, such that the concentric rings of one layer overlap the annular spaces between the concentric rings of the immediately adjacent layer.

DESCRIPTION OF THE PREFERRED EMBODIMENTS

Figure 1:
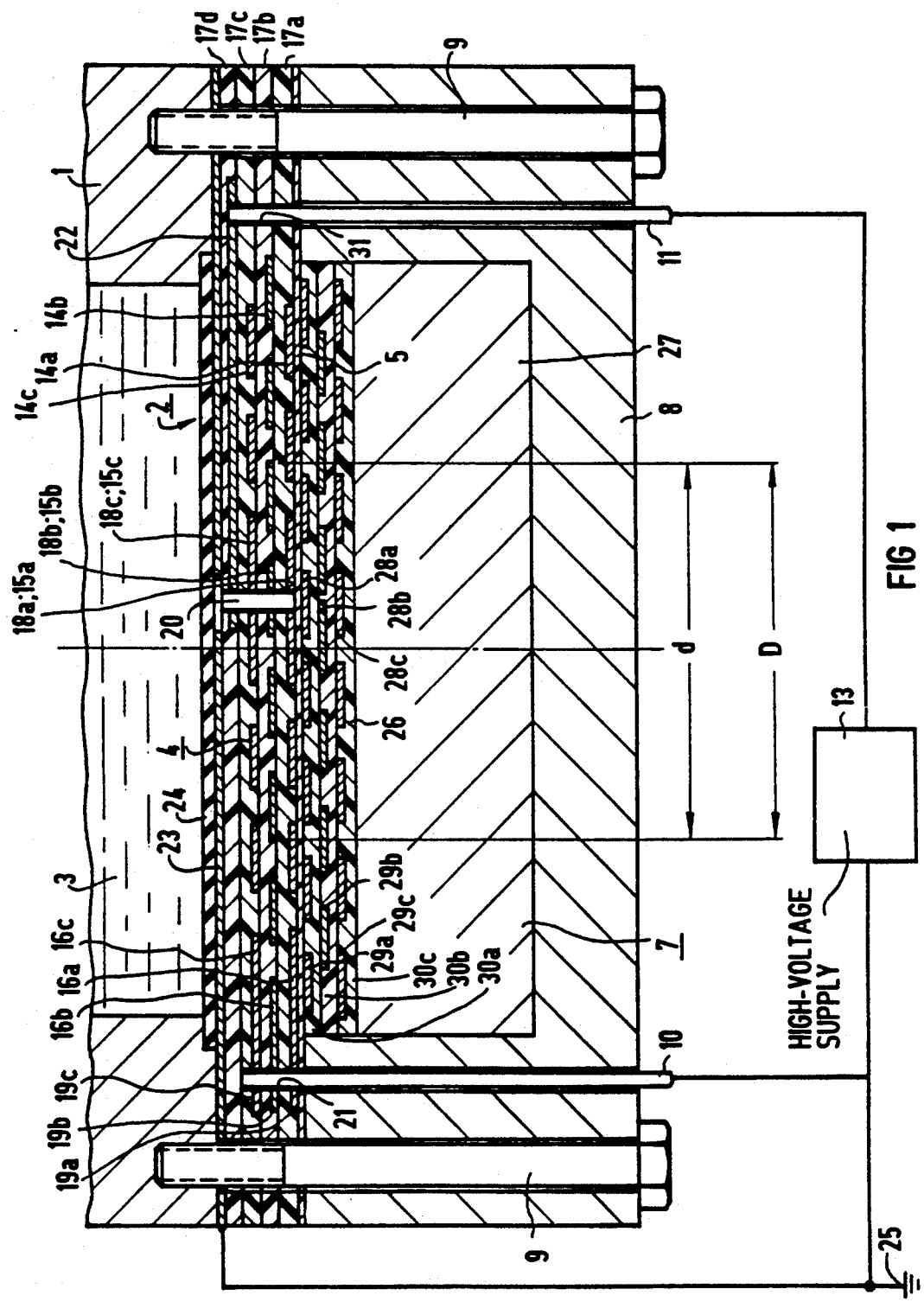
FIG. 1 is a longitudinal sectional view taken through a shockwave source constructed in accordance with the principles of the present invention.

A shockwave source constructed in accordance with the principles of the present invention, as shown in the exemplary embodiment of FIG. 1, includes a substantially tubular 1 (only partially shown in FIG. 1) which has a space 3 filled with a liquid serving as an acoustic propagation medium for shockwaves. One end of the space 3 is closed or covered by a membrane 2. The membrane 2 contains a coil arrangement 4, having spiral turns. The membrane 2 containing the coil arrangement 4 is disposed opposite a stationary element 7, in the form of a circular disc, with an insulating foil 5 disposed between the membrane 2 and the stationary element 7. The stationary element 7 is received in a large recess in a holder 8 consisting of electricity insulating material, for example ceramic. The membrane 2 containing the coil arrangement 4, the insulating foil 5 and the holder 8 containing the stationary element 7 are secured to the housing 1 with bolts 9 such that the edge of the membrane 2 and the edge of the insulating foil 5 are clamped between the holder 8 and the housing 1. The coil arrangement 4 is connected to a schematically-indicated high-voltage supply 13 via conductors 10 and 11 which exit to the exterior of the holder 8 through respective bores therein.

The coil arrangement 4 is charged with high-voltage pulses for generating shockwaves from the high-voltage supply 13. As a consequence of the pulse-like currents flowing through the coil arrangement 4, oppositely directed currents induced in the electrically conductive material of the stationary element 7. The respective currents in the coil arrangement 4 and the stationary element 7 have electromagnetic fields respectively associated therewith, which are also oppositely directed, so that the membrane 2 containing the coil arrangement 4 is suddenly repelled by the stationary element 7, resulting in the formation of a shockwave in the liquid in the space 3.

In the shockwave source shown in FIG. 1, the membrane 2 is a multi-layer structure containing a plurality of windings, namely three windings 14a, 14b and 14c, which are electrically insulated from each other and connected in parallel with each other, forming the coil arrangment 4. The windings 14a, 14b and 14c are respectively disposed in a corresponding plurality of layers, i.e., three layers. For clarity, only the innermost and outermost turns of the windings 14a, 14b and 14c are provided with reference numerals in FIGS. 1 and 2. The innermost turns are referenced 15a, 15b and 15c, and the outermost turns are referenced 16a, 16b and 16c. The winding 14a is the winding which is immediately adjacent to the stationary element 7, and the winding 14c is the winding which is farthest from the stationary element 7. All turns of the windings 14a, 14b and 14c have a substantially constant width B. The windings 14a, 14b and 14c of the individual layers are arranged offset relative to each other so that the turns of the winding of one layer completely overlap the spiral space between the turns of the winding of the immediately adjacent layer. In the illustrated exemplary embodiment, the arrangement of the layers is selected so that the average radius of curvature of the spiral space at arbitrary locations of the coil arrangement 4 corresponds to the average radius of curvature of the turn which overlaps the spiral space at all locations, as shown by example for a location of the coil arrangement 4 in FIG. 2 with reference to the average radii of curvature r and R.

The turns of the individual windings 14a, 14b and 14c are formed by metal foil, for example copper or silver foil. The turns of the windings 14a, 14b and 14c are respectively attached to that side of insulator foils 17a, 17b and 17c facing toward the stationary element 7. The connection of the windings 14a, 14b and 14c to the insulator foils 17a, 17b and 17c can be made, for example, by gluing. The insulator foils 17a, 17b and 17c together with the windings 14a, 14b and 14c respectively connected thereto are joined together in a planar format, for example by gluing.

As stated above, the windings 14a, 14b and 14c of the coil arrangement 4 are connected in parallel. For this purpose, the innermost turns 15a, 15b and 15c of the windings 14a, 14b and 14c are respectively provided with contact pads 18a, 18b and 18c, all penetrated by a bore 20. The outermost turns 16a, 16b and 16c of the windings 14a, 14b and 14c are respectively provided with contact pads 19a, 19b and 19c all penetrated by a bore 21. The bores 20 and 21 also extend through the insulator foils 17a, 17b and 17c. The bores 20 and 21 are "through-connected" in the manner as is used in printed circuit board technology to make multi-layer printed circuits, so that the windings 14a, 14b and 14c are electrically connected to each other in the respective regions of their contact pads 18a, 18b and 18c, and the contact pads 19a, 19b and 19c. A further insulator foil 17d has a side facing toward the stationary element 7 which is provided with an interconnect 22 formed of metal foil, which proceeds radially outwardly from the center of the membrane. This interconnect 22 is also penetrated by the bore 20. A through-connected bore 31 extends radially outside the outermost turns 16a, 16b and 16c and through the insulator foils 17a, 17b, 17c and 17d, into which the conductor 11 is soldered. The conductor 10 is soldered in the bore 21. The insulator foil 17d is completely covered by an electrically conductive coating 23, for example a metal foil glued to the insulator foil 17d. The conductive coating 23 is separated from the interconnect 22 by the insulator foil 17d. At its side facing toward the acoustic propagation medium, the coating 23 is provided with a layer 24 of cavitation-resistant material, for example rubber. The layer 24 can be joined to the coating 23, for example, by a glued connection. To reduce the interference emitted during operation of the shockwave source, the coating 23 is connected to a shielding potential, such as ground potential 25. This can be accomplished by grounding one terminal of the high-voltage supply 13, as shown in the exemplary embodiment of FIG. 1.

The stationary element 7 has a region 26 neighboring the coil arrangement 4 which is also in the form of a multi-layer structure, containing a plurality of electrically conductive sections which are electrically insulated from each other, and respective arranged in a plurality of layers. There are three layers in the exemplary embodiment of FIG. 1. The region 26 of the stationary element 7 which is in the form of a multilayer structure is joined, for example by gluing, to a base member 27 of the stationary element 7, which is formed of electrically conductive material, for example copper. For clarity, only the innermost and outermost conductive sections of the individual layers are provided with reference numerals in FIGS. 1 and 3. The innermost sections are referenced 28a, 28b and 28c and the outermost sections are referenced 29a, 29b and 29c. The sections 28a and 29a are the conductive sections which are immediately adjacent to the coil arrangement 4. The sections 28c and 29c are the sections which are farthest from the coil arrangement 4.

All conductive sections, with the exception of the innermost section 28b of the middle layer, which has a circular shape, are in the form of rings having a substantially identical width b, which are concentric with the central axis M of the shockwave source.

The conductor sections of the individual layers are arranged offset relative to each other so that the concentric rings of one layer completely overlap the annular spaces between the conductive sections of the immediately adjacent layer. In the illustrated exemplary embodiment, the arrangement of the layers is selected such that the average diameter of an annular space corresponds to the average diameter of the conductive section which overlaps that annular space, as shown for an exemplary space and electrically conductive section in FIG. 2, referenced with average diameters d and D. The conductive sections are formed of metal foil, for example copper or silver foil, and are attached, for example by gluing, on the respective sides of insulator foils 30a, 30b and 30c facing toward the coil arrangement 4. The individual layers formed by the insulator foils 30a, 30b and 30c, having the electrically conductive sections applied thereon, are joined to each other in a planar format, for example by gluing.

Figure 2:
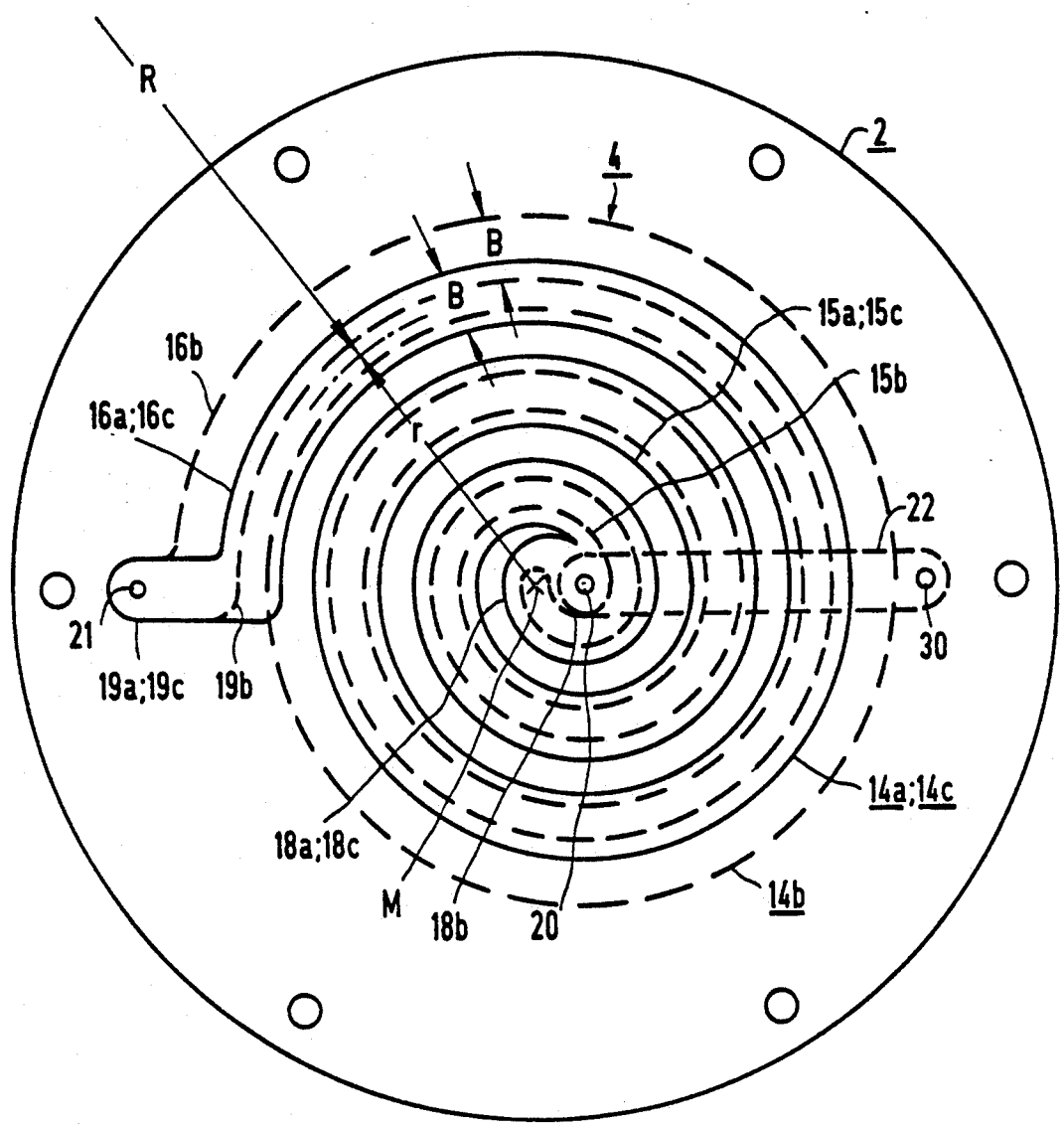
FIG. 2 is a plan view of the membrane containing the coil arrangement in the shockwave source of FIG. 1.
Figure 3:
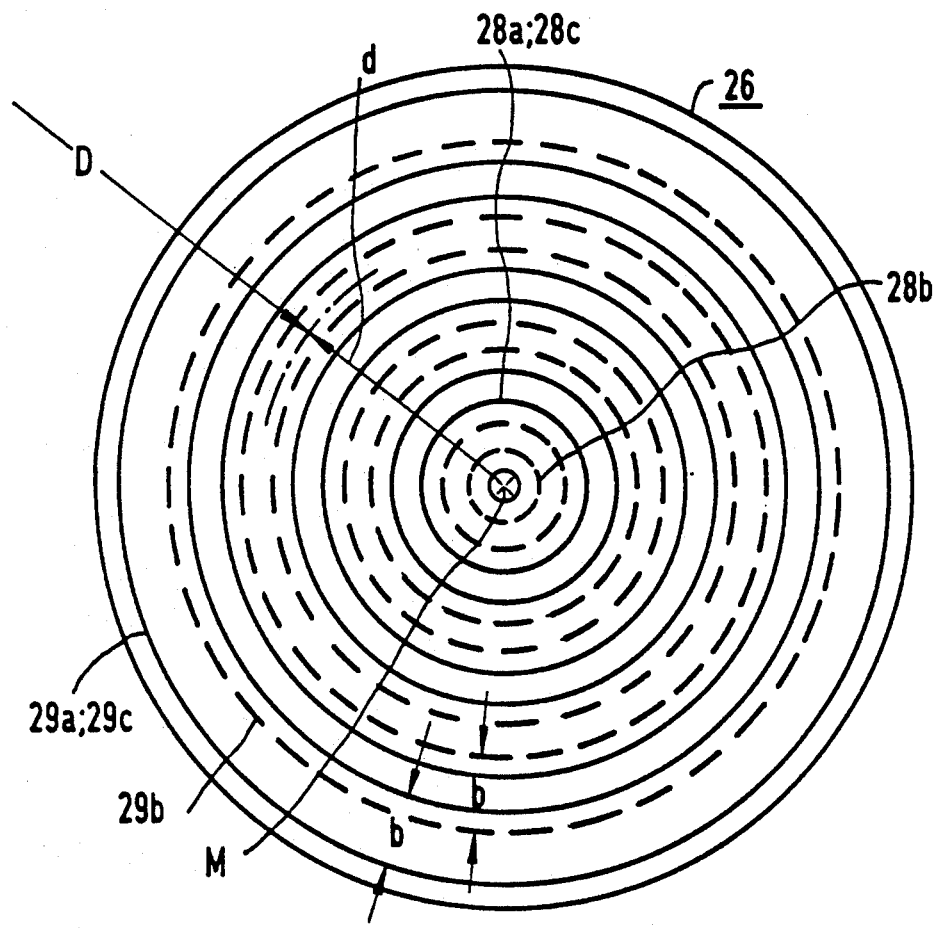
FIG. 3 is a plan view of the stationary element of the shockwave source of FIG. 1.

In the exemplary embodiment shown in FIGS. 1 and 2, the windings 14a of the layer of the membrane 2 immediately adjacent the stationary element 7, and the windings 14c of the layer of the membrane 2 farthest from the from the stationary element 7, are congruent. This is shown in FIG. 2, which is a view of that side of the membrane 2 facing toward the stationary element 7, wherein the winding 14a, shown with solid lines, is also provided with the reference numeral for the winding 14c. Analogously, the electrically conductive sections of the layer of the region 26 of the stationary element 7 which is immediately adjacent to the coil arrangement 4, and the layer of the region 26 of the stationary element 7 which is farthest from the coil arrangement 4 are congruent. This is illustrated in FIG. 3, which shows a view of that side of the region 26 facing the coil arrangement 4, wherein the conductive sections of the layer immediately adjacent to the coil arrangement 4 are shown with solid lines, and are also provided with the reference numerals 28c and 29c associated with the layer farthest from the coil arrangement 4. If more than three layers are provided, it is recommended to arrange the conductive sections or the windings (generically referred to herein as conductive elements), so that the conductive elements of odd-numbered layers are congruent with each other, and the conductive elements of even-numbered layers are congruent.

Figure 4:
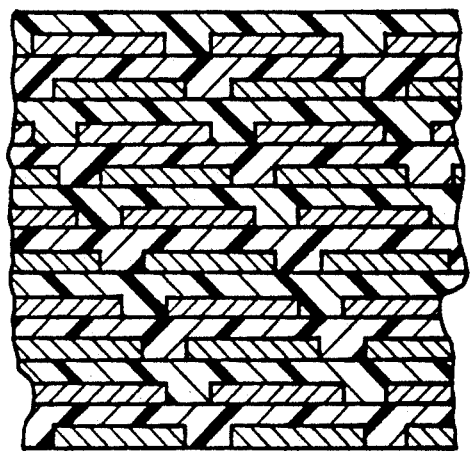
FIGS. 4 and 5 are side sectional views showing details of further embodiments of portions of the shockwave source shown in FIG. 1.

As an alternative to the illustrated arrangement, it is possible to arrange the conductive elements of the individual layers of the coil arrangement 4 and the region 26 of the stationary element 7 so that the conductive elements in a particular layer only partially overlap the spaces between the conductive elements of the immediately adjacent layer. In this embodiment, for example as shown in FIG. 4, the electrically conductive elements of a particular layer would completely overlap the space between the conductive elements of only one other layer, and this would not be an adjacent layer. A coincidence of the average diameters d and D, or the radii of curvature r and R, in the manner set forth in conjunction with FIGS. 1 through 3 would be established in the embodiment of FIG. 4, for the first and fifth layers, for the second and sixth layers, for the third and seventh layers, etc. A congruent arrangement of the conductive elements would be established for the first and the ninth layers, for the second and the tenth layers, for the third and the eleventh layers, etc.

A beneficial, especially low-scatter curve of the magnetic and electrical field lines is achieved due to the layered structure of the coil arrangement contained in the membrane 2 and in the region 26 of the stationary element 7. An improved electromagnetic interaction between the coil arrangement 4 of the membrane 2 and the stationary element 7 results, enabling improved efficiency in the conversion of electrical energy into acoustic energy. A further improvement in the electromagnetic interaction, and thus in the efficiency, is achieved by the overlap of the turns of the windings 14a, 14b and 14c of the coil arrangement 4 in the above-described manner, because this results in an extremely uniform electromagnetic field. Another improvement in the efficiency, and thus in the service life, of the shockwave source is achieved by the overlap of the electrically conductive sections in the region 26 of the stationary element 7. Capacitive coupling of the conductive sections with each other is thereby achieved, resulting in uniformly distributed differences in potential being present between the individual conductive sections, so that the risk of voltage arcing is substantially suppressed. A uniform division or distribution of the differences in potential can be further promoted by a conductive connection (not shown) of the conductive section 28a to the conductor 11, and of the conductive section 29a to the conductor 10.

The thicknesses of the windings 14a, 14b and 14c, of the insulator foils 17a, 17b, 17c and 17d, of the coating 23, of the layer 24, of the conductive sections and of the insulator layers 30a, 30b, 30b and 30c are shown greatly exaggerated in FIG. 1 for clarity. Additionally, the conductive sections and the winding turns are shown as being received into the respective insulator foils so that a planar surface results. This need not necessarily be so in the practical construction of the shockwave source since the thickness of the conductive sections and of the windings can be extremely small, for example less than $10^{-4}$ m. In this case, the adhesive layers (not shown in the figures) which are provided for joining the individual layers can accommodate and compensate for the slightly non-planar surfaces. Moreover, the individual layers can be manufactured by photolithographic methods, similar to the manufacture of a printed circuit, such as by etching an electrically conductive layer, for example a copper layer, laminated to an electrically insulating plastic foil or layer.

As a consequence of the coating 17 being connected to ground potential 25 as a shielding potential, the shockwave source is effective shielded so that RF interference emitted by the shockwave source is substantially reduced. This effect is enhanced if the housing 1 consists of electrically conductive material, and also lies at ground potential 25 as a consequence of being in contact with the coating 23.

Figure 5:
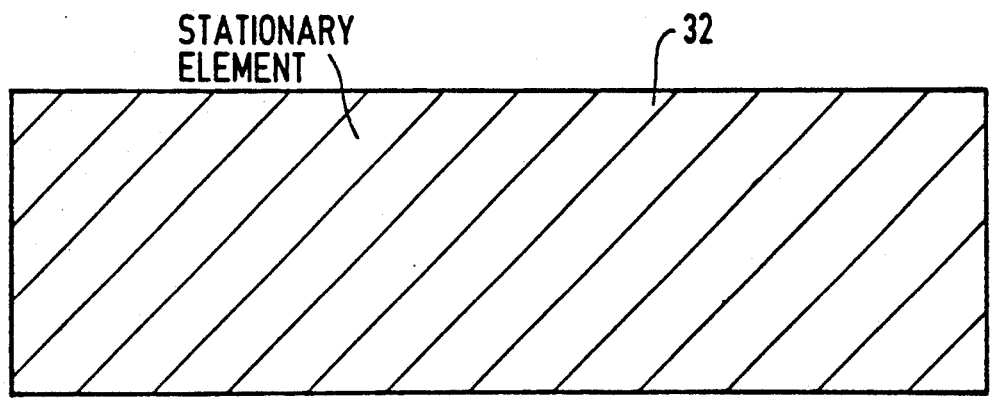

Departing from the described exemplary embodiment, the stationary element 7 need not necessarily have a region 26 fashioned as a multilayer structure and containing electrically conductive sections. A circular disc member of electrically conductive material, for example copper, may be used as the stationary element 7. Such a member 32 is shown in FIG. 5, which can be used in the shockwave source of FIG. 1 instead of the stationary element 7 having the region 26.

In the above-described exemplary embodiment, the windings 14a, 14b and 14c of the individual layers, and the conductive sections of the individual layers, are arranged in surfaces parallel to each other. It is also possible, however, to provide those elements on spherically curved surfaces, for example, instead of planar surfaces, resulting in a shockwave source having a membrane and a coil arrangement which are spherically curved in a known manner, for example for focusing the shockwaves.

Although modifications and changes may be suggested by those skilled in the art, it is the intention of the inventor to embody within the patent warranted hereon all such changes and modifications as reasonably and properly come within the scope of his contribution to the art.

I claim as my invention:

1. An electrodynamic shockwave source comprising:
    a housing containing an acoustic propagation medium;
    a stationary element containing electrically conductive material disposed in said housing;
    coil means movably disposed in said housing for interacting with said acoustic propagation medium and consisting of a membrane carrying a plurality of electrically conductive windings connected in parallel and otherwise insulated from each other, said membrane consisting of a plurality of layers and said windings being respectively disposed in said layers of said membrane; and
    charging means for charging only said coil means with a pulse for causing rapid repulsion of said coil means from said stationary element to generate an acoustic shockwave in said propagation medium.

2. An electrodynamic acoustic shockwave source as claimed in claim 1 wherein said electrically conductive windings in each layer of said membrane are arranged with spaces therebetween, and wherein the electrically conductive windings of a layer of said membrane at least partially overlap the spaces in an adjacent layer.

3. An electrodynamic acoustic shockwave source as claimed in claim 2 wherein said winding in each layer of a plurality of successive layers of said membrane is a spiral formed by a plurality of winding turns with a spiral space between said winding turns, and wherein said windings in said successive layers of said membrane are arranged offset relative to each other so that the winding turns of a layer overlap the spiral space in an adjacent layer.

4. An electrodynamic acoustic shockwave source as claimed in claim 3 wherein said electrically conductive windings in said layers of said membrane are arranged in a plurality of parallel surfaces.

5. An electrodynamic acoustic shockwave source as claimed in claim 4 wherein said surfaces are planar.

6. An electrodynamic acoustic shockwave source as claimed in claim 1 further comprising an electrically conductive coating disposed on a side of said coil means facing away from said stationary element and electrically insulated from said coil means, and connected to a source of shielding potential.

7. An electrodynamic shockwave source comprising:
a housing containing an acoustic propagation medium;
coil means movably disposed in said housing for interacting with said acoustic propagation medium;
a stationary element disposed in said housing and containing electrically conductive material, at least in a region disposed adjacent said coil means, in the form of electrically conductive sections insulated from each other and arranged in a plurality of region layers; and
charging means for charging only said coil means with a pulse for causing rapid repulsion of said coil means from said stationary element to generate an acoustic shockwave in said propagation medium.

8. An electrodynamic shock wave source as claimed in claim 7 wherein said electrically conductive sections in each region layer are arranged with spaces therebetween, and wherein the electrically conductive sections in a region layer at least partially overlap the spaces in an adjacent region layer.

9. An electrodynamic shock wave source as claimed in claim 8 wherein each region layer of a plurality of successive region layers includes a plurality of concentric rings forming said electrically conductive sections, separated by annular spaces, and wherein said concentric rings in said successive region layers are offset relative to each other so that the concentric rings of a region layer at least partially overlap the annular spaces of an adjacent region layer.

10. An electrodynamic shock wave source as claimed in claim 7 wherein said electrically conductive sections of said region layers are arranged in a plurality of parallel surfaces.

11. An electrodynamic shock wave source as claimed in claim 10 wherein said surfaces are planar.

12. An electrodynamic acoustic shockwave source comprising:
a housing containing an acoustic propagation medium;
a stationary element containing electrically conductive material disposed in said housing and having a region consisting of electrically conductive sections insulated from each other and disposed in a plurality of region layers; and
coil means movably disposed in said housing adjacent said region for interacting with said acoustic propagation medium by rapid repulsion from said stationary element to generate an acoustic shockwave in said propagation medium when said coil means is charged with a current pulse, said coil means consisting of a membrane carrying a plurality of electrically conductive windings connected in parallel and otherwise electrically insulated from each other, said membrane consisting of a plurality of layers and said electrically conductive windings being respectively disposed in said layers of said membrane.

13. An electrodynamic acoustic shockwave source as claimed in claim 12 wherein said electrically conductive sections in each region layer are arranged with spaces therebetween, and wherein the electrically conductive sections in a region layer at least partially overlap the spaces in an adjacent region layer.

14. An electrodynamic acoustic shockwave source as claimed in claim 12 wherein each region layer of a plurality of successive region layers includes a plurality of concentric rings forming said electrically conductive sections, separated by annular spaces, and wherein said concentric rings in said successive region layers are disposed offset relative to each other so that the concentric rings of a region layer overlap the annular spaces of an adjacent region layer.

15. An electrodynamic acoustic shockwave source as claimed in claim 12 wherein said electrically conductive windings in each layer of said membrane are arranged with spaces therebetween, and wherein the electrically conductive windings of a layer of said membrane at least partially overlap the spaces in an adjacent layer.

16. An electrodynamic acoustic shockwave source as claimed in claim 15 wherein said winding in each layer of a plurality of successive layers of said membrane is a spiral formed by a plurality of winding turns with a spiral space between said winding turns, and wherein said windings in said successive layers of said membrane are arranged offset relative to each other so that the winding turns of a layer overlap the spiral space in an adjacent layer.

17. An electrodynamic acoustic shockwave source as claimed in claim 12 wherein said electrically conductive sections in said region layers and said electrically conductive windings in said membrane layers are arranged in a plurality of parallel surfaces.

18. An electrodynamic acoustic shockwave source as claimed in claim 17 wherein said surfaces are planar.

19. An electrodynamic acoustic shockwave source as claimed in claim 12 further comprising an electrically conductive coating disposed on a side of said coil means facing away from said stationary element and electrically insulated from said coil means, and connected to a source of shielding potential.

* * * * *